(12) United States Patent
Cogan et al.

(10) Patent No.: US 11,596,787 B2
(45) Date of Patent: Mar. 7, 2023

(54) PERIPHERAL NERVE ELECTRODE FOR NEURAL RECORDING AND STIMULATION

(71) Applicant: Board of Regents, The University of Texas System, Austin, TX (US)

(72) Inventors: Stuart F. Cogan, Dallas, TX (US); Atefeh Ghazavi, Dallas, TX (US); Alexandra Joshi-Imri, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 86 days.

(21) Appl. No.: 16/835,180

(22) Filed: Mar. 30, 2020

(65) Prior Publication Data
US 2020/0306527 A1 Oct. 1, 2020

Related U.S. Application Data

(60) Provisional application No. 62/825,712, filed on Mar. 28, 2019.

(51) Int. Cl.
*A61N 1/05* (2006.01)
*A61N 1/36* (2006.01)

(52) U.S. Cl.
CPC ........ *A61N 1/0556* (2013.01); *A61N 1/36064* (2013.01); *A61N 1/36067* (2013.01); *A61N 1/36071* (2013.01); *A61N 1/36096* (2013.01); *A61N 1/36117* (2013.01)

(58) Field of Classification Search
CPC ........ A61B 5/388; A61B 5/4041–4052; A61N 1/0556
See application file for complete search history.

(56) References Cited

U.S. PATENT DOCUMENTS

| | | | | |
|---|---|---|---|---|
| 3,157,181 A | * | 11/1964 | McCarty | A61N 1/0551 607/118 |
| 2004/0006281 A1 | * | 1/2004 | Matsukawa | A61B 5/24 600/544 |
| 2010/0029149 A1 | * | 2/2010 | Malloy | H01R 9/05 439/888 |
| 2013/0072808 A1 | * | 3/2013 | Neves | A61B 5/6868 600/544 |
| 2016/0067497 A1 | * | 3/2016 | Levine | A61N 1/36139 607/62 |
| 2016/0235329 A1 | * | 8/2016 | Bernstein | A61B 5/05 |
| 2017/0172437 A1 | * | 6/2017 | Butera | A61N 1/0556 |

(Continued)

FOREIGN PATENT DOCUMENTS

DE 102004031377 A1 * 2/2006 ........... A61B 5/04

OTHER PUBLICATIONS

English translation of DE 102004031377 A1 (Year: 2006).*
(Continued)

*Primary Examiner* — Eric D. Bertram
(74) *Attorney, Agent, or Firm* — Yee & Associates, P.C.

(57) ABSTRACT

A bioelectric interface is provided. The bioelectric interface comprises a case having a channel configured to hold a nerve. An electrode array is slidably coupled to the case, wherein the electrode array comprises a number of electrode shanks. The case restricts movement of the electrode array to one degree of freedom toward or away from the nerve held in the channel for insertion of the electrode shanks into the nerve.

9 Claims, 17 Drawing Sheets

(56) References Cited

U.S. PATENT DOCUMENTS

| | | | | |
|---|---|---|---|---|
| 2018/0125427 A1* | 5/2018 | Oh | ................ | A61N 1/0558 |
| 2018/0368712 A1* | 12/2018 | Gardner | ................ | C23C 16/325 |
| 2019/0060638 A1* | 2/2019 | Oh | ................ | A61B 17/3468 |

OTHER PUBLICATIONS

Yim et al. "Handheld Nerve Electrode Insertion Tool." Oct. 2018. IEEE/ASME Transactions on Mechatronics, vol. 23, No. 5, pp. 2525-2530. (Year: 2018).*

Pesantez et al., "Wet release of multipolymeric structures with a nanoscale release layer," Sensors and Actuators B: Chemical, vol. 132, Issue 2, Jun. 16, 2008, pp. 426-430.

Vitale et al., "Fluidic Microactuation of Flexible Electrodes for Neural Recording," Nano Lett. 2018, 18, pp. 326-335. https://pubs.acs.org/doi/10.1021/acs.nanolett.7b04184.

\* cited by examiner

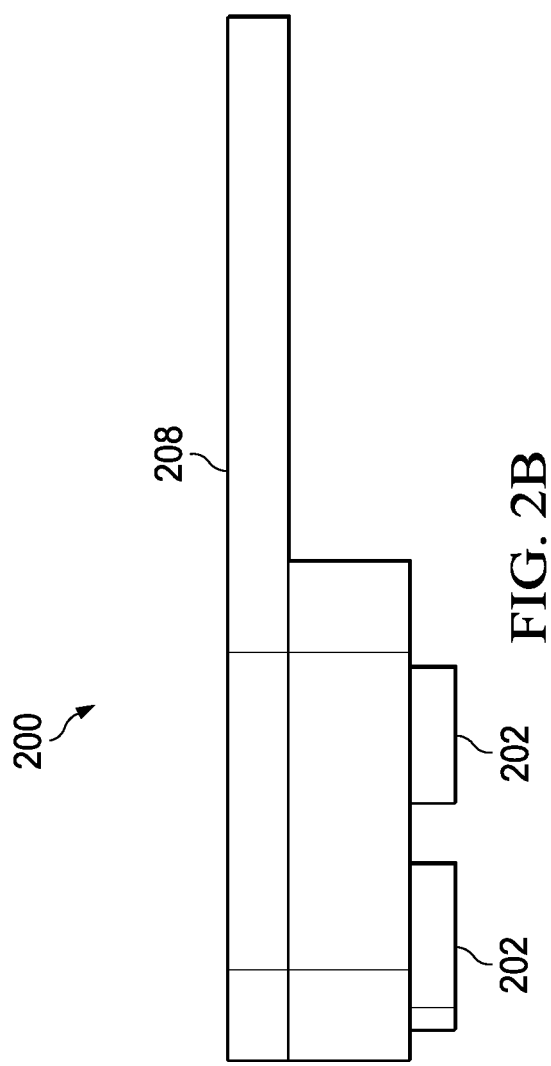

PERIPHERAL NERVE ELECTRODE FOR NEURAL RECORDING AND STIMULATION

RELATED APPLICATION

This application claims priority to U.S. Provisional Application 62/825,712, filed Mar. 28, 2019, the entirety of which is hereby incorporated by reference.

STATEMENT OF GOVERNMENT INTEREST

This invention was made with government support under Contract No. U01 NS090454 awarded by the National Institutes of Health. The government has certain rights in the invention.

BACKGROUND INFORMATION

1. Field

The present disclosure relates generally to medical devices, and more specifically to a device and method for the insertion of microelectrodes into peripheral nerves.

2. Background

Bioelectronic interfaces provide a means of recording and stimulating neural activity in nerves. Improved selectivity of stimulation and recording can be achieved with microelectrode-based bioelectronic interfaces when the microelectrodes are inserted directly into nerves. Such an interface allows the selective stimulation of the nerves by an electrical device. Conversely, such a bioelectric interface might also receive signals selectively from within the nerve and communicate these signals to an electronic device.

Such bioelectronic interfaces might provide treatments for issues such as pain control or assistance with motor control impairment in cases of disease or injury. Such bioelectronic interfaces may further provide treatments for epilepsy, depression, hypertension, and heart failure.

SUMMARY

An illustrative embodiment provides a bioelectric interface. The bioelectric interface comprises a case having a channel configured to hold a nerve fiber. An electrode array is slidably coupled to the case, wherein the electrode array comprises a number of electrode shanks. The case restricts movement of the electrode array to one degree of freedom toward or away from the nerve fiber held in the channel for insertion of the electrode shanks into the nerve fiber.

Another illustrative embodiment provides a bioelectric interface that comprises a lower section of a case and an upper section of the case, wherein the lower section and upper section of the case together enclose a channel configured to hold a nerve. At least one electrode array comprising one or more electrode shanks of different lengths is slidably sandwiched between the lower section and upper section of the case. The case restricts movement of the electrode array to one degree of freedom toward or away from the nerve held in the channel for insertion of the electrode shanks into the nerve.

Another illustrative embodiment provides a method of forming a bioelectric interface. The method comprises placing a nerve in a channel formed in a case, wherein the case comprises a lower section and an upper section that enclose the channel. A number of shanks of an electrode array are inserted into the nerve in the channel. The electrode array is slidably sandwiched between the lower section and upper section of the case, and wherein the case restricts movement of the electrode array to one degree of freedom toward or away from the nerve held in the channel for insertion of the electrode shanks into the nerve.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 2B illustrates a side view of the upper portion of the nerve holder case in accordance with an illustrative embodiment;

DETAILED DESCRIPTION

The illustrative embodiments recognize and takes into account that bioelectric interfaces allow the stimulation of the nerves by electrical devices and can be used to provide treatments for issues such as pain control or assistance with impaired motor control, and treatments for epilepsy, depression, hypertension, and heart failure, among others.

The illustrative embodiments also recognize and takes into account that insertion of microelectrode arrays into a nerve often results in buckling of the electrode shanks due to mechanical resistance of the nerve tissue and the delicate structure of the electrode shanks.

The illustrative embodiments also recognize and takes into account that insertion of microelectrodes into nerves can also produce foreign body responses due to excessive displacement of tissue and trauma during surgical implantation.

The illustrative embodiments provide a bioelectronics interface structure that acts as a stable intraneural interface for the peripheral nerves, especially nerves with small dimensions. A microelectrode array (MEA) is sandwiched between top and bottom parts of the interface structure that form a nerve holder case. The MEA might be retracted initially to allow the nerve to be placed inside a nerve channel contained within the structure. Subsequently, the MEA, which has only one degree of translational freedom, can be inserted into the nerve and locked in place. During insertion, the user slides the MEA forward into the nerve, and the position of the MEA is guided and stopped by posts implemented inside the structure.

The nerve holder case provides a channel within which the nerve is placed. The channel stabilizes the position of the nerve with respect to the electrode shanks. This feature ensures that during surgical implantation the electrode shanks can be inserted into the nerve with the desired orientation of the shanks with respect to the nerve and to the desired depth within the nerve with a high degree of precision. Once inserted into the nerve, the electrode shanks are prevented from moving within the nerve. This locational stability reduces movement-related exacerbation of any foreign body response to the implanted MEA and further improves the long-term stability of a functional response elicited by stimulation and improves the reliability of neural recording by minimizing relative motion.

In an embodiment, the structure is made of two parts, top and bottom. In order to integrate the top and bottom part of the structure four posts are designed at the top part that will be inserted into four openings of the bottom part. This three-dimensional attachment of the parts helps to provide better adhesion and integrity by increasing the attached surface area and providing a mechanical barrier for separation.

The nerve holder case structure further acts as a protective cover to prevent the electrode shanks from getting damaged during implantation and handling.

Figure 1A:
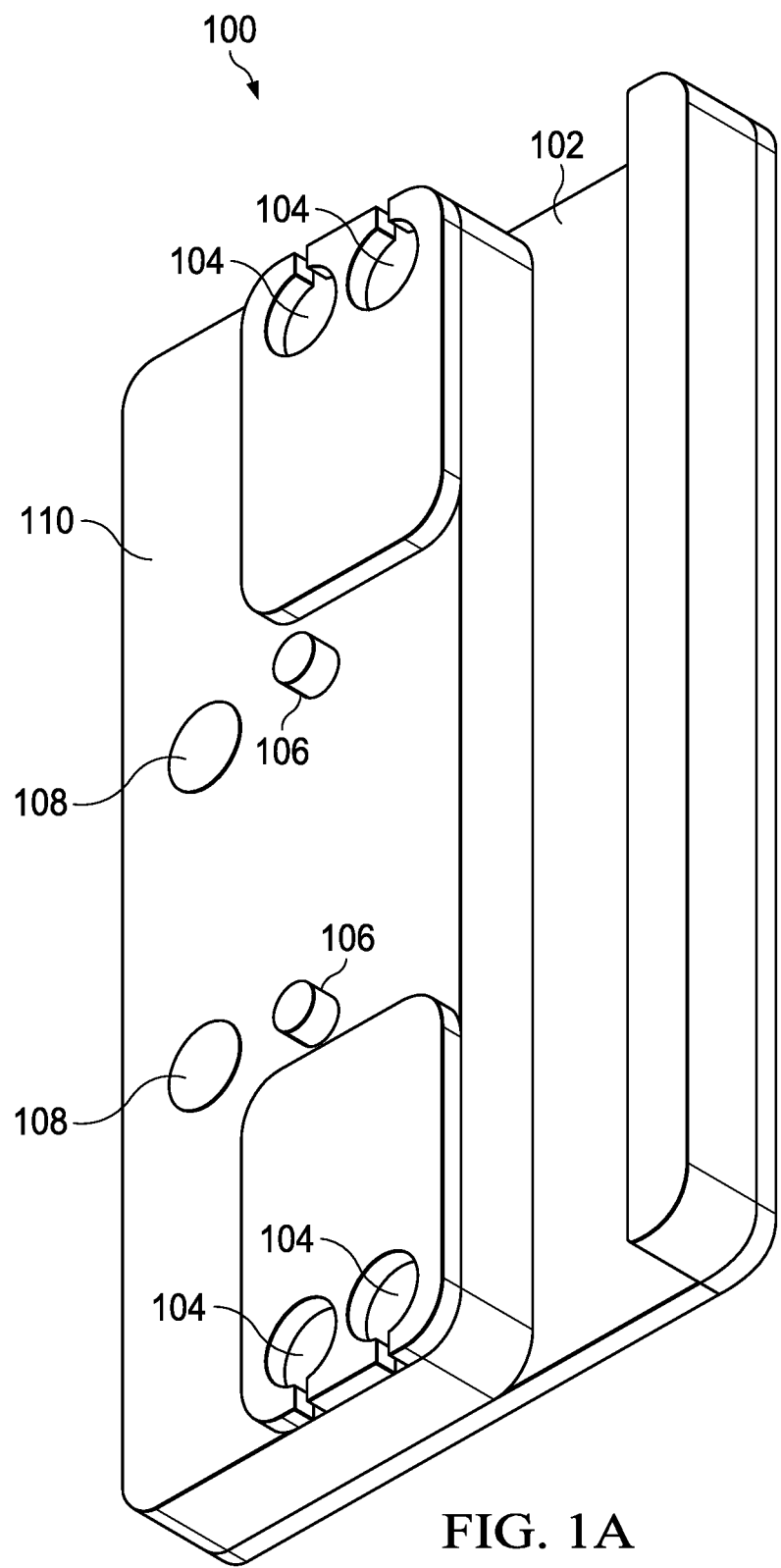
FIG. 1A illustrates a perspective view of a lower portion of a nerve holder case in accordance with an illustrative embodiment.
Figure 1B:
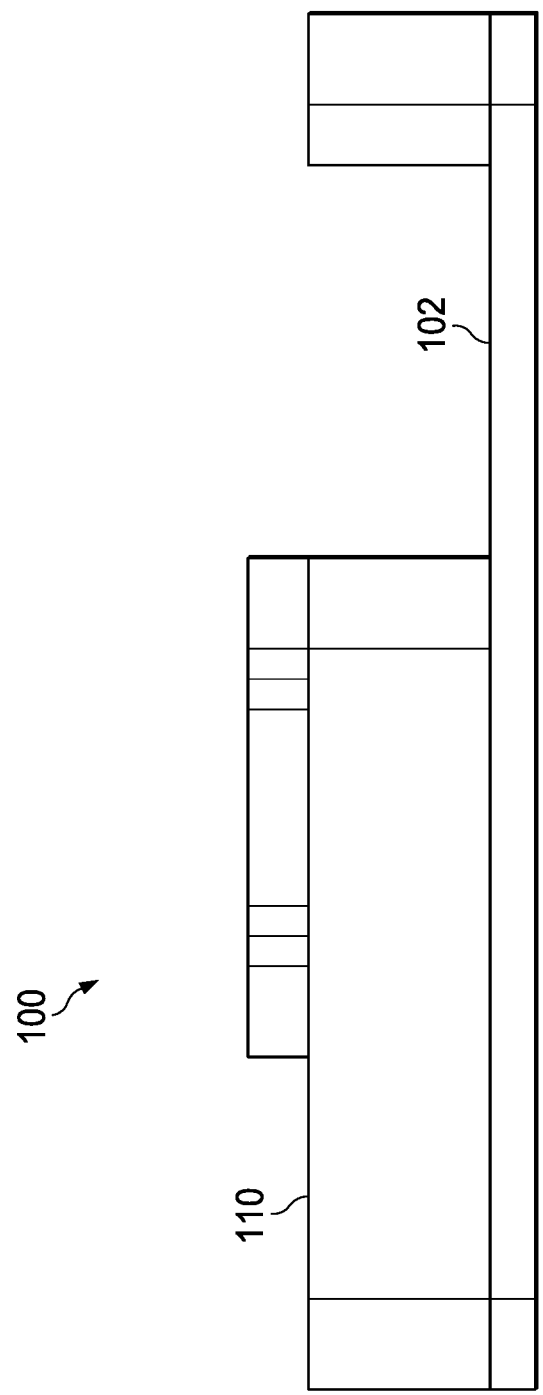
FIG. 1B illustrates a side view of the lower portion of the nerve holder case in accordance with an illustrative embodiment.

FIG. 1A illustrates a perspective view of a lower portion 100 of a nerve holder case in accordance with an illustrative embodiment. FIG. 1B illustrates a side view of the lower portion 100 of the nerve holder case in accordance with an illustrative embodiment.

The lower portion or section 100 of the nerve holder case comprises a channel 102 for locating the nerve. The depth of the channel 102 is designed such that the nerve will fit into it while maintaining its physical dimensions. The lower portion 100 also comprises two posts 106 configured to restrict movement of an electrode array in one direction (towards and away from the nerve), explained below.

Figure 6A:
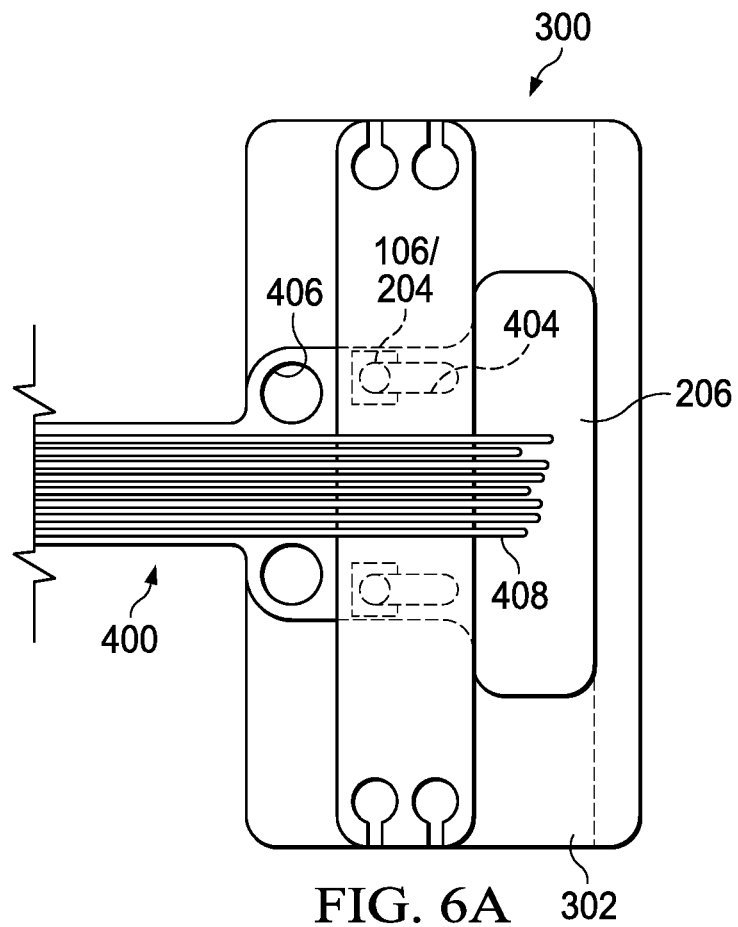
FIG. 6A illustrates a close top plan, cross-section view of a nerve holder case with a coupled electrode array in accordance with an illustrative embodiment.
Figure 6B:
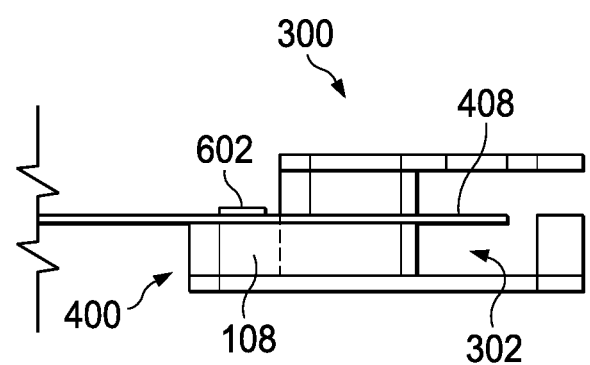
FIG. 6B illustrates a side, cross-section view of the nerve holder case with the coupled electrode array in accordance with an illustrative embodiment.

During assembly, an electrode array 400 (see FIGS. 4A and 4B) can be placed on the surface 110 of the lower portion 100, and elongate (e.g., elliptical) loops (openings) on the electrode array are mounted on the posts 106 of the nerve holder case (see FIGS. 6A and 6B).

Figure 2A:
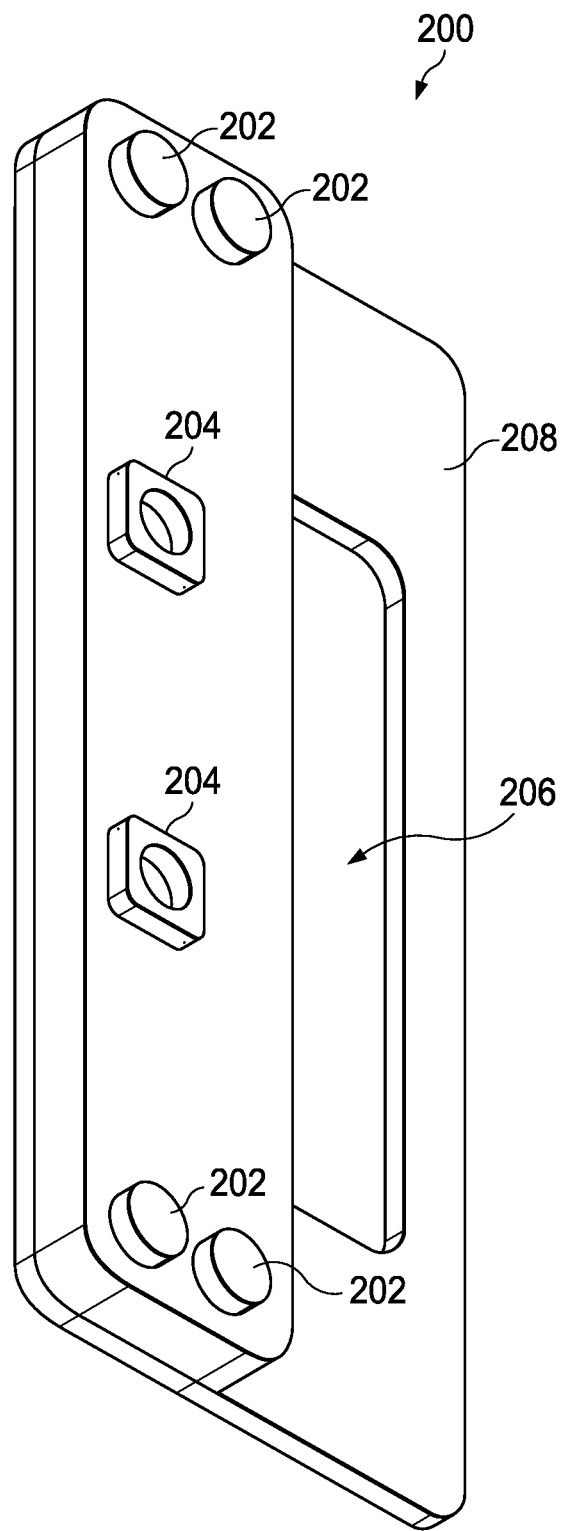
FIG. 2A illustrates a perspective view of an upper portion of a nerve holder case in accordance with an illustrative embodiment.

In the present example, lower portion 100 comprises holes 104 (two on each side) configured to secure the lower portion to the upper portion 200 of the nerve holder case (see FIGS. 2A and 2B). The number of holes 104 can vary depending on the size of the holder case and electrode array. Holes 104 can be filled with, e.g., moisture and heat resistive glue, wherein posts 202 on the upper portion 200 of the nerve holder case can be placed into holes 104 to hold the lower portion 100 and upper portion 200 together.

Lower portion 100 of the nerve holder case might also comprise circular post holes 108 that are configured to be filled with material, e.g., silicone posts, after insertion of the electrode array into a nerve to secure the position of the electrode array with respect to the nerve after insertion (see FIGS. 6A and 6B).

FIG. 2A illustrates a perspective view of an upper portion 200 of a nerve holder case in accordance with an illustrative embodiment. FIG. 2B is a side view of the upper portion 200 of the nerve holder case in accordance with an illustrative embodiment.

Upper portion or section 200 of the nerve holder case comprises features that mate with corresponding features of lower portion 100. In the present example, upper portion 200 comprises posts 202 (two on each side) that fit into holes 104 in lower portion 100. As explained above, posts 202 can be secured in holes 104 by an adhesive such as moisture and heat resistive glue.

Similarly, raised notches 204 in upper portion 200 are configured to receive posts 106 on lower portion 100. Notches 204 prevent the electrode array 400 from moving perpendicular to the surface of the array (along the axis of posts 106) and thereby restrict array movement to one degree of freedom toward or away from the nerve. Such electrode movement along the post's axis is limited to a distance slightly greater than the electrode thickness in the axial direction. Typically, such distances are 1 μm to 50 μm larger than the thickness of the electrode array itself.

Figure 14:
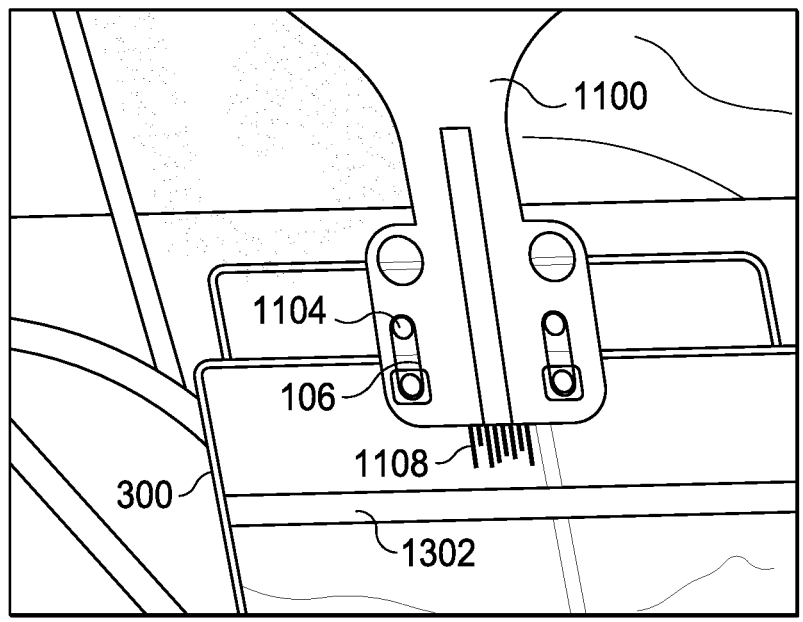
FIG. 14 illustrates a nerve held in a nerve holder case before insertion of electrodes in accordance with an illustrative embodiment.

Cover plate 208 of upper portion 200 optionally includes a window 206 that allows a user to see the electrode shanks when the array and holder case are fully assembled (see FIGS. 6A and 14). Window 206 allows the user to monitor insertion of the electrodes into the nerve.

Figure 3A:
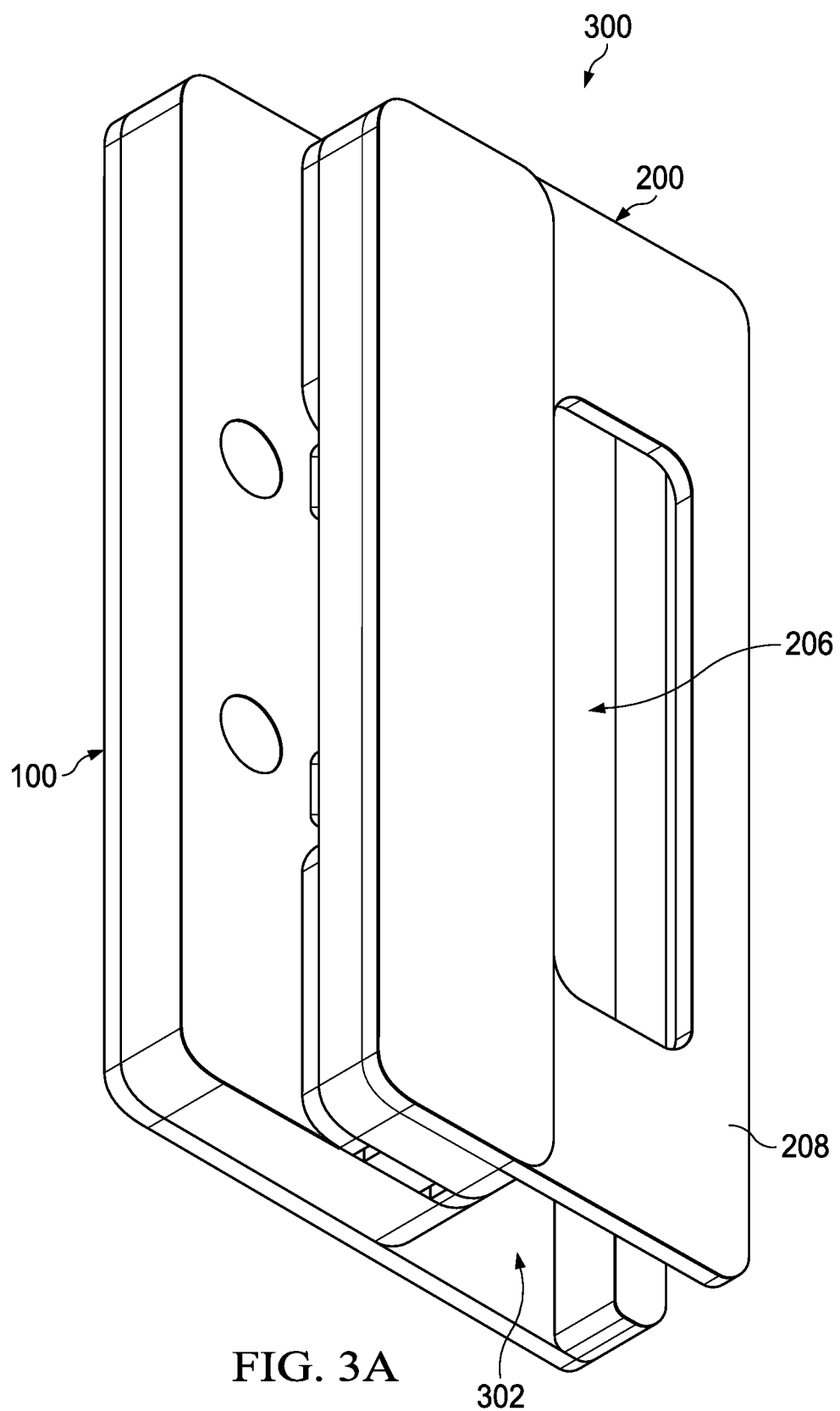
FIG. 3A illustrates a perspective view of an assembled nerve holder case, including both upper and lower potions, in accordance with an illustrative embodiment.
Figure 3B:
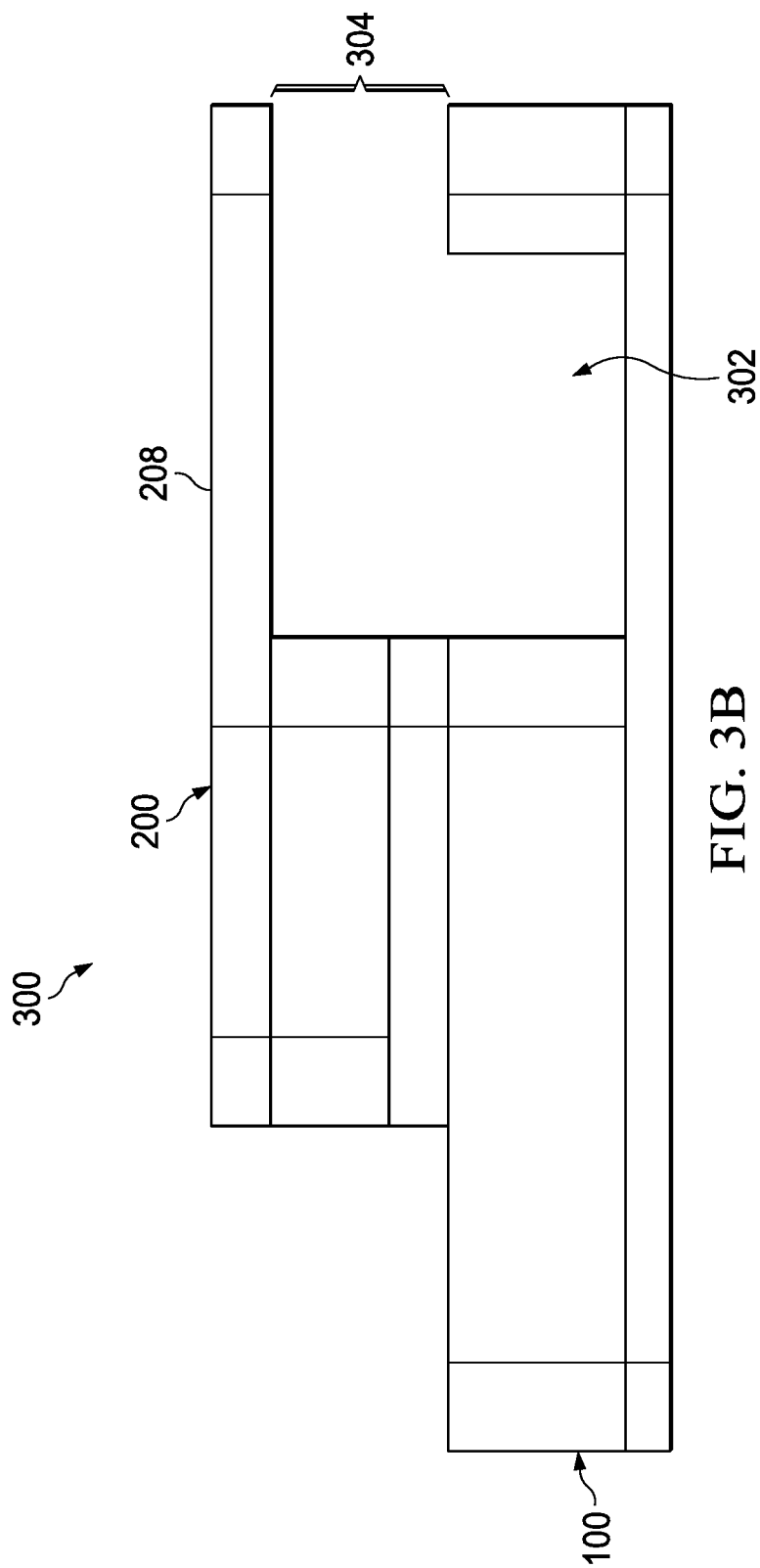
FIG. 3B illustrates a side view of the assembled nerve holder case in accordance with an illustrative embodiment.

FIG. 3A illustrates a perspective view of an assembled nerve holder case 300, including both upper and lower potions, in accordance with an illustrative embodiment. FIG. 3B is a side view of the assembled nerve holder case 300 in accordance with an illustrative embodiment.

When lower portion 100 and upper portion 200 are combined to form the assembled nerve holder case 300, the channel 102 of lower portion 100 and cover plate 208 of upper portion 200 form covered channel 302. A nerve can be located into covered channel 302 through opening 304 and held in place in the covered channel 302 during insertion of the electrodes (see FIGS. 14 and 15). Opening 304 is smaller than the nerve diameter such that the nerve can be squeezed into the channel 302 while preventing it from sliding out of the channel.

The nerve holder case 300 is small (e.g., 800 µm width) and has a low mass. These features minimize damage to the nerve during implantation and minimize damage to the nerve from forces applied to the case from surrounding tissue that may move relative to the nerve such as, e.g., muscle.

It should be noted that an electrode array (e.g., 400) would be positioned in place on lower portion 100 before upper portion 200 is secured in place. However, assembled nerve holder case 300 is shown in FIGS. 3A and 3B without the electrode array for easier illustration of the complementarity between lower portion 100 and upper portion 200.

The nerve holder case 300 advantageously allows the insertion into nerve of ultramicroelectrode arrays (UMEAs). An ultramicroelectrode array will have at least one electrode site interfacing to the neural tissue within the nerve wherein at least one dimension of the electrode is less than 20 µm and preferably less than 10 µm.

Figure 4A:
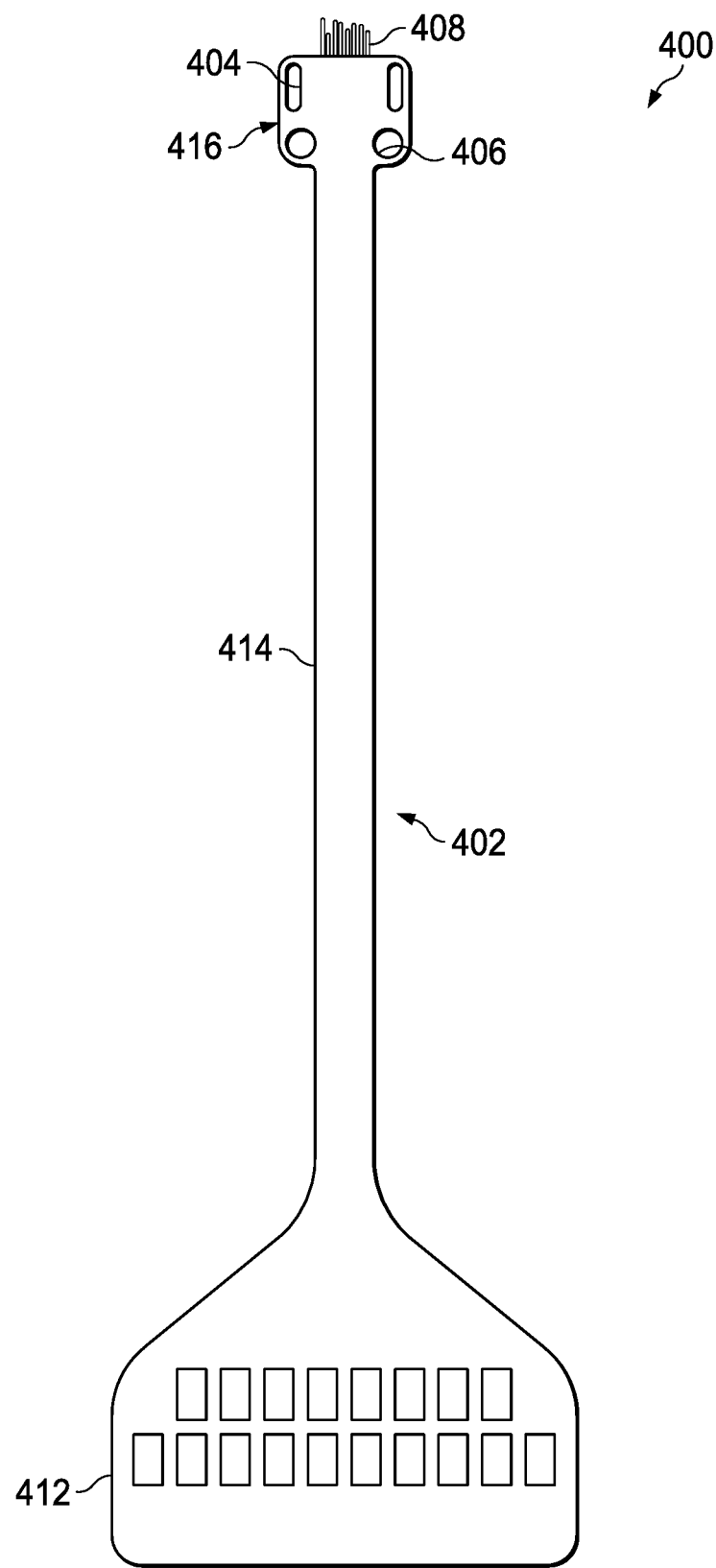
FIG. 4A illustrates a bottom plan view of an electrode array in accordance with an illustrative embodiment.
Figure 4B:
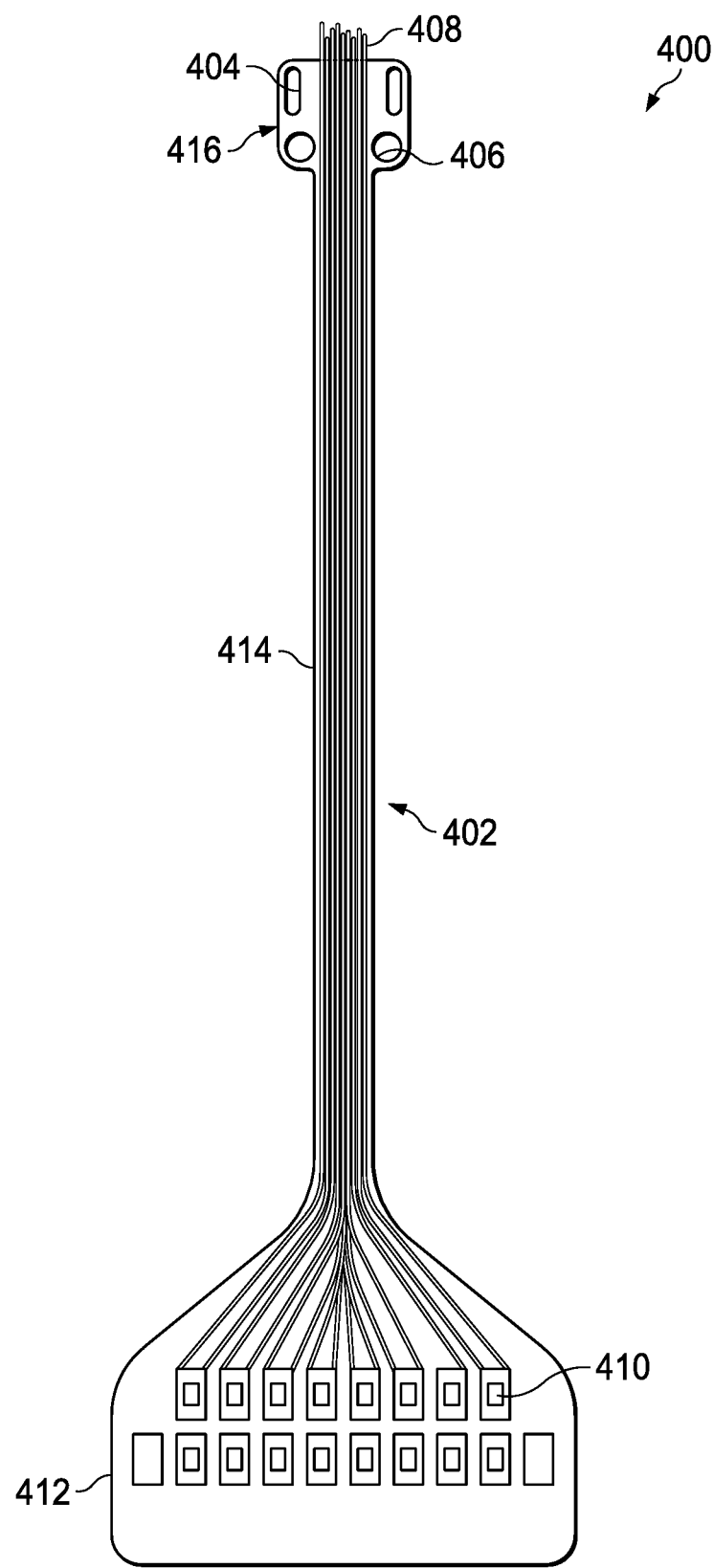
FIG. 4B illustrates a top plan view of the electrode array in accordance with an illustrative embodiment.

FIG. 4A illustrates a top plan view of an electrode array 400 in accordance with an illustrative embodiment. FIG. 4B illustrates a bottom plan view of the electrode array 400 in accordance with an illustrative embodiment.

Electrode array 400 comprises an electrode holder 402 that holds a number of microelectrode shanks 408. Electrode array 400 might be an example of an UMEA, having a thickness of less than 10 microns (µm). In the illustrative example shown in FIGS. 4A and 4B, array holder 402 comprises a wide base 412 that comprises a number of metal bond pads 410 (shown in FIG. 4B). Metal bond pads 410 are provided at the proximal end 412 to allow electrical connection of electrical circuitry to the electrode array 400, thereby providing electrical signals for neural stimulation or to recording electrical signals that originate within the nerve.

In the illustrative example, base 412 tapers into a neck 414 along which electrode shanks 408 run. The length of array neck 414 can vary depending on the anatomical area of application (see FIGS. 11A and 11B).

The head 416 of electrode holder 402 is configured to couple the electrode array 400 to nerve holder case 300. The head 416 comprises elongate loops 404 that are configured to slide along raised notches/posts 204/106 of the nerve holder case 300 during insertion of shanks 408 into a nerve.

The flexible electrode array 400 can be fabricated from amorphous silicon carbide with gold metal traces that terminate in electrode sites at the distal end of the electrode that penetrates into the target nerve.

The head 416 of the electrode holder 402 also comprises a number of circular loops 406 that are configured to align with post holes 108 in lower portion 100 when the electrode array is moved into the forward position to insert shanks 408 into a nerve (see FIG. 6A).

As depicted in the drawings, electrode array 400 might optionally comprise shanks 408 that are a number of different lengths. The different lengths of shanks 408 distribute electrode sites across as much of a nerve bundle (fascicle) as possible to ensure that the desired nerve function is accessed by the electrode array 400. For example, a nerve fascicle might include both afferent neural fibers that carry signals to the central nervous system and efferent neural fibers that carry signals from the central nervous system. The medical application in question might be directed toward only one of these functions or both. The different lengths of shanks 408 allows electrode contact across the width of the nerve to ensure contact with the desired neural fibers.

The typical direction of MEA or UMEA insertion will be perpendicular to the longitudinal axis of the nerve, although device designs that provide "offnormal" insertion of the electrode shanks into the nerve may usefully be used to place the electrode shanks at different depths within the nerve.

Figure 5:
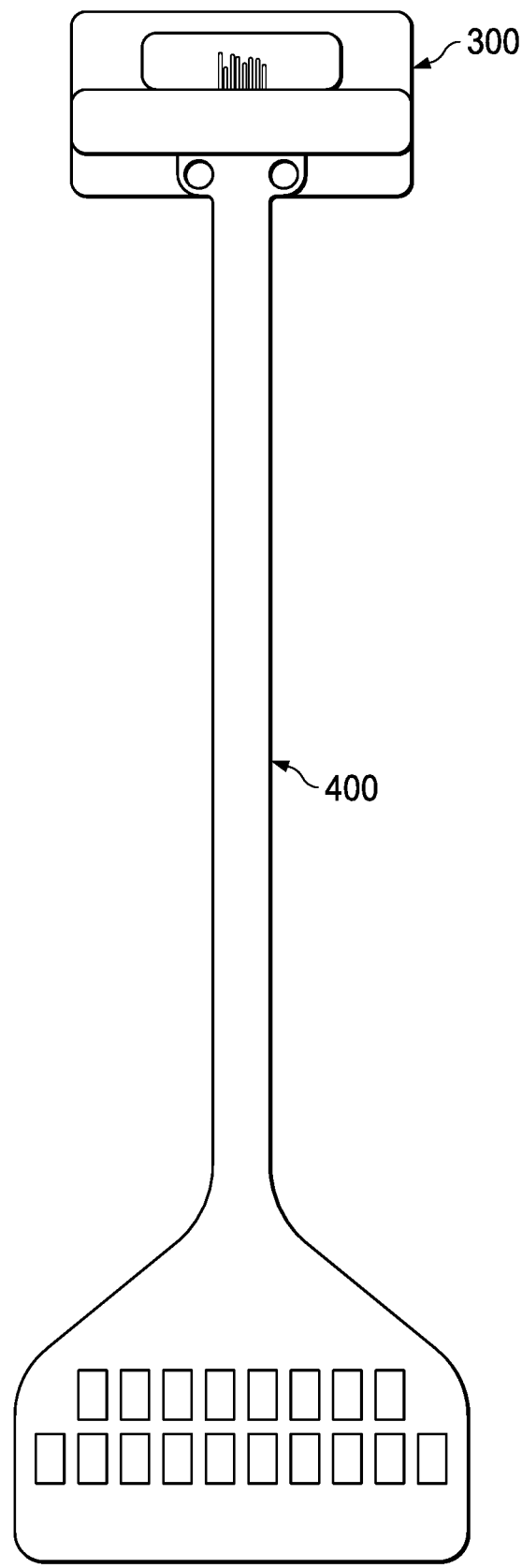
FIG. 5 illustrates a nerve holder case coupled with an electrode array in accordance with an illustrative embodiment.

FIG. 5 illustrates a nerve holder case 300 coupled with an electrode array 400 in accordance with an illustrative embodiment. As mentioned above, the electrode array 400 is sandwiched between the lower portion 100 and upper portion 200 of nerve holder case 300 before the upper and lower portions are secured to each other. The electrode array 400 is slidably coupled to the case 300, wherein the case 300 restricts movement of the electrode array 400 to one degree of freedom toward or away from the nerve fiber held in the channel 102 for insertion of electrode shanks 408 into the nerve fiber.

In an embodiment (not shown) two or more array structures can be stacked one-upon-the-other and sandwiched between the lower portion 100 and upper portion 200 of the nerve holder case 300. Stacking the electrode arrays in this manner allows the penetration into the nerve of a three-dimensional distribution of electrode shanks to better access the neural organization within the nerve. In this embodiment, the slot within the nerve holder case 300 can be made slightly larger than the thickness of the stack of arrays.

For example, a three-layer electrode array can be designed to be integrated with the nerve holder case structure. The electrode shanks on the top, middle, and bottom layer of the array may be configured with different lengths such that the distribution of lengths on the top, middle, and bottom layers advantageously distribute electrode sites within the totality of the cross-section of the nerve. In a related embodiment, the electrode shanks on the top, middle and bottom layers are configured to bend upward, straight and downward such that the inserted electrodes access an even greater portion of the nerve cross-section. This configuration of layers in the three-dimensional electrode array provides accessibility of the shanks to the fibers at different depths within a nerve cross section, while minimizing the space occupied by the array in the nerve. The bending direction of the layers may be achieved by engineering the fabrication process to control the distribution of residual stresses within the array such that the balance of stresses of the fabricated layers will cause the shanks of the array to bend upward, remain straight or bend downward as the shanks are inserted into the nerve.

FIG. 6A illustrates a close top plan, cross-section view of a nerve holder case 300 with a coupled electrode array 400 in accordance with an illustrative embodiment. FIG. 6B illustrates a side, cross-section view of the nerve holder case 300 with the coupled electrode array 400 in accordance with an illustrative embodiment.

The nerve holder case 300 may be provided with a catch located in one or both of the top and bottom members of the case that allows the array 400 to slide in the direction of insertion into the nerve but not to retract from the nerve once the penetration is of the desired deep into the nerve. The advantages of this feature are that the array 400 does not inadvertently retract from the nerve during implantation. In addition, the electrode shanks 408 remain at the desired depth within the nerve, and a sealant or adhesive need not be applied to the nerve holder case 300 to prevent retraction of the array 400.

As shown in FIG. 6A, the posts 106/notches 204 are positioned inside the elongate loops 404 in the array 400, allowing the array to slide along in the nerve holder case 300 to insert the electrode shanks 408 into a nerve, while also limiting the distance the array 400 can slide within the case 300. FIG. 6A shows the electrode array 400 in the forward position (i.e. position of nerve insertion) within the nerve holder case 300. In this position, circular loops 406 in the array 400 align with post holes 108 in the lower portion 100 of case 300. Once the electrode is inserted into the nerve, holes 108 can be filled with a material such as silicone to form posts 602 that protrude through circular loops 406 to lock the array 400 in the forward position (see sequence in FIGS. 14 and 15) in order to lock the electrode inside the nerve.

The nerve holder case 300 provides a slot that has a height slightly greater than the thickness of the UMEA 400. The electrode shanks 408 are constrained to move in only one plane by the nerve holder case 300 and therefore cannot buckle during insertion into the nerve. The advantage of the ultramicroelectrode dimension is that such electrodes minimize or avoid the well-known foreign body response that is detrimental to the neural recording or stimulation performance of the electrode array. The individual electrode shanks 408 might be, e.g., 8 µm thick and 23 µm wide.

Figure 7A:
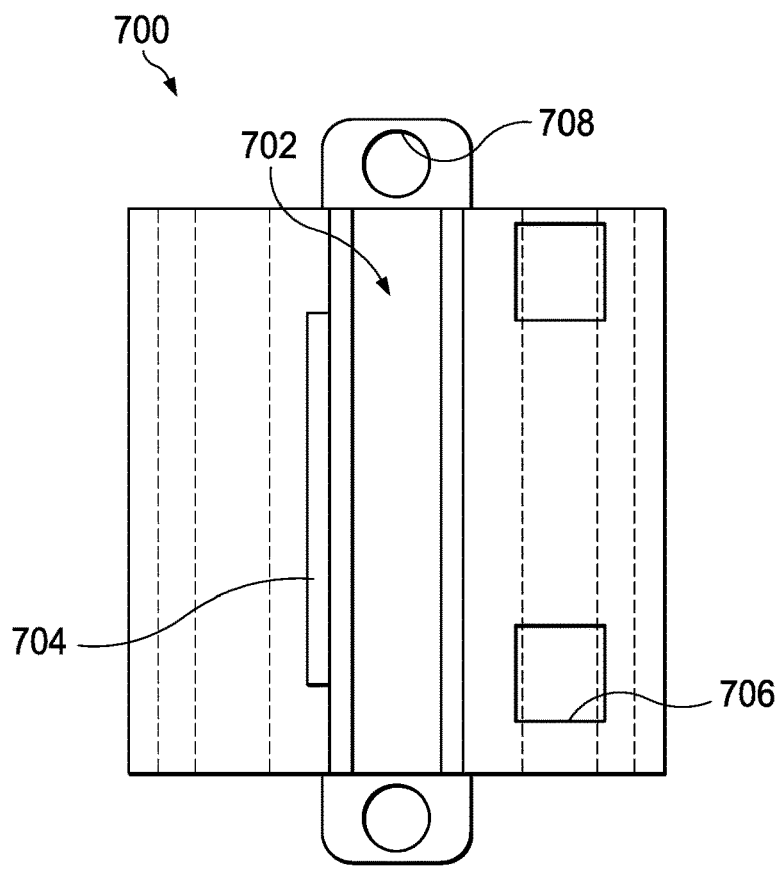
FIG. 7A illustrates a top plan view of a nerve holder case in accordance with an illustrative embodiment.
Figure 7B:
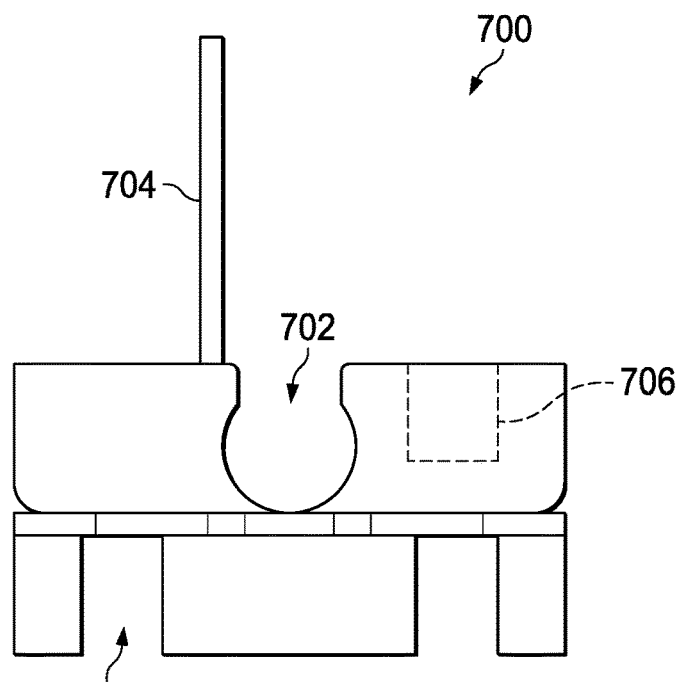
FIG. 7B illustrates a side view of the nerve holder case in accordance with an illustrative embodiment.

FIG. 7A illustrates a top plan view of a nerve holder case 700 in accordance with an illustrative embodiment. FIG. 7B illustrates a side view of the nerve holder 700 in accordance with an illustrative embodiment.

Figure 8A:
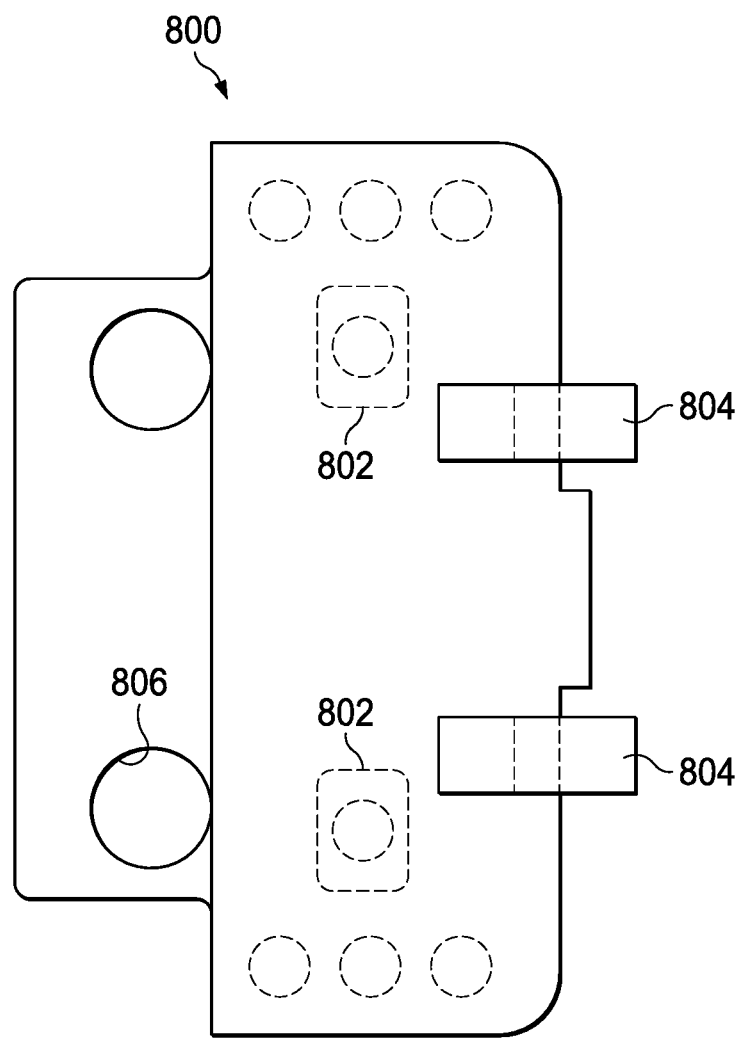
FIG. 8A illustrates a top plan view of an array holder in accordance with an illustrative embodiment.
Figure 8B:
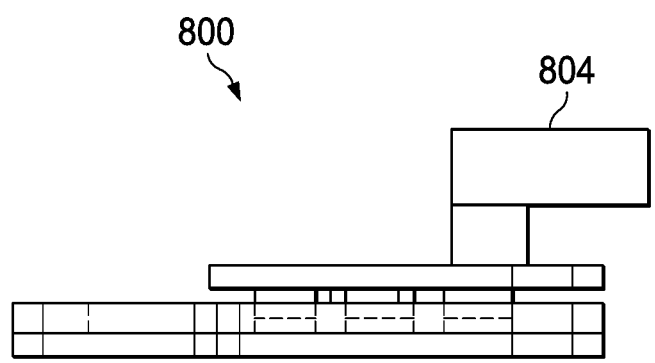
FIG. 8B illustrates a side view of the array holder in accordance with an illustrative embodiment.

FIG. 8A illustrates a top plan view of an array holder 800 in accordance with an illustrative embodiment. FIG. 8B illustrates a side view of the array holder 800 in accordance with an illustrative embodiment. Nerve holder 700 and array holder 800 comprise an alternate embodiment two-part nerve holder case.

A nerve is located in channel 702. Guide surface 704 is used to guide the electrode array holder 800 into position (See FIG. 9). Post notches 706 accommodate posts 804 of array holder 800, allowing the array holder 800 to be secure in place after a nerve has been located in channel 702.

Nerve holder 700 may optionally be configured to have suture loops 708 that permit the holder to be fixed to tissue at the time of implantation using sutures that are threaded through the hole within the loop.

Similar to holder case 300, array holder 800 comprises posts 802 that control the movement of an electrode array along one directional axis. Likewise, holes 806 are configured to align with circular loops (e.g., 406) in the electrode array when it is in the forward position and can be filled with material (e.g., silicone) to lock the array in the forward position.

Figure 9:
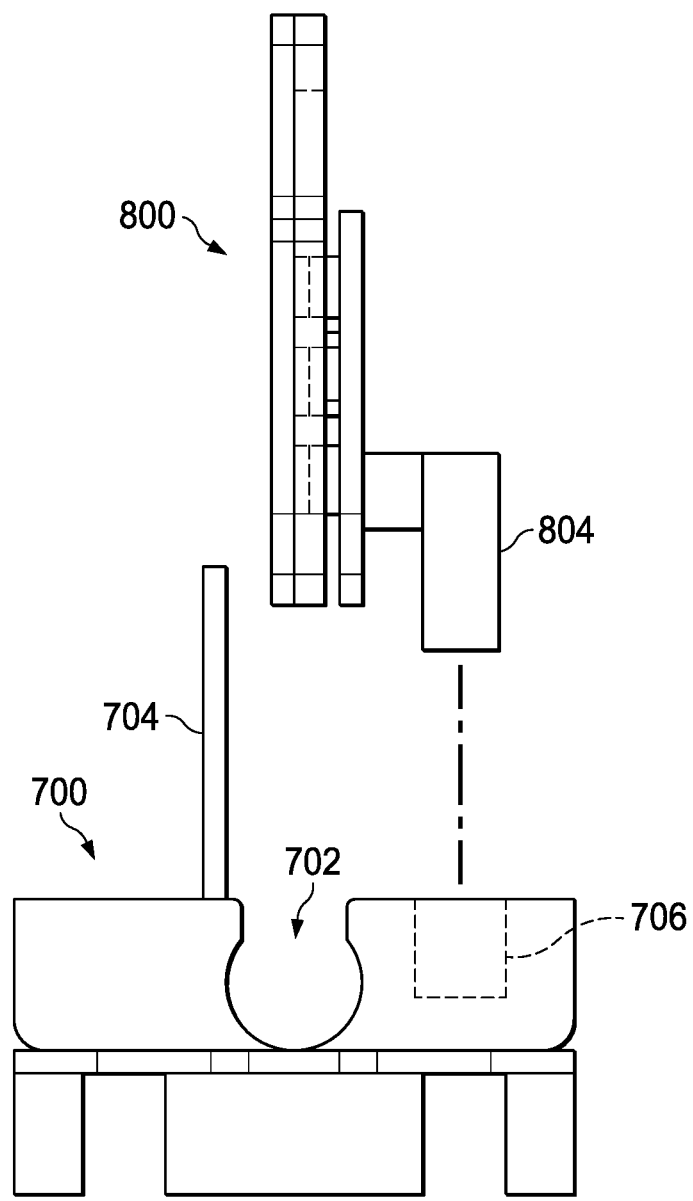
FIG. 9 illustrates a side view depicting how the nerve holder couples to the electrode holder in accordance with an illustrative embodiment.

FIG. 9 illustrates a side view depicting how the nerve holder 700 couples to the electrode holder 800 in accordance with an illustrative embodiment. Array holder 800 is guided down surface 704, and posts 804 are inserted into notches 706.

Figure 10A:
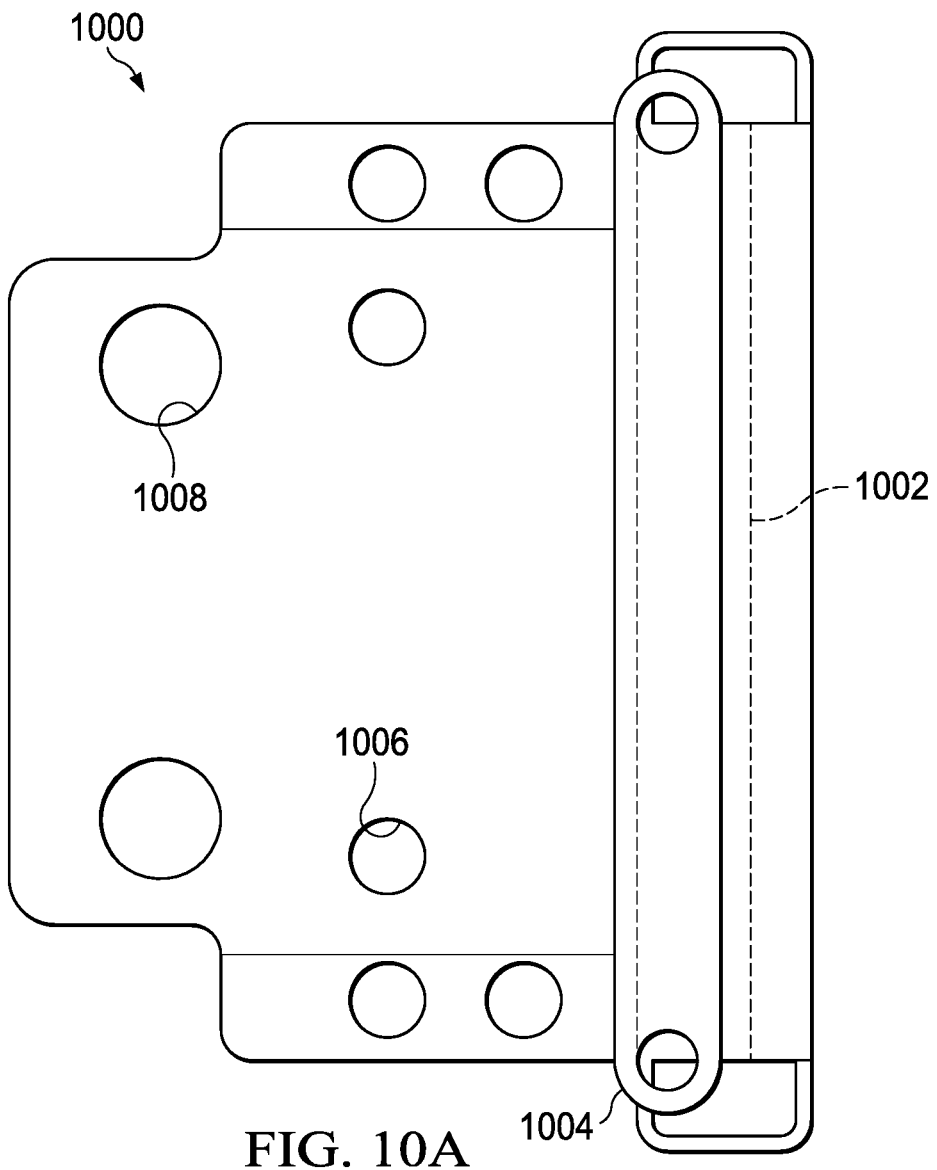
FIG. 10A illustrates a top plan view of a one-piece nerve and electrode array holder in accordance with an illustrative embodiment.
Figure 10B:
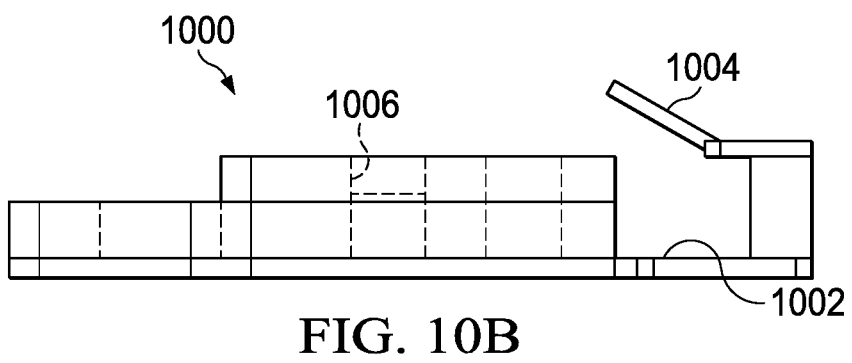
FIG. 10B illustrates a side view of the one-piece nerve and electrode array holder in accordance with an illustrative embodiment.

FIG. 10A illustrates a top plan view of a one-piece nerve and electrode array holder 1000 in accordance with an illustrative embodiment. FIG. 10B illustrates a side view of the one-piece nerve and electrode array holder 1000 in accordance with an illustrative embodiment.

Holder 1000 is an alternate embodiment in which the channel 1002 where the nerve is placed is accessible via a hinged cover 1004 than can be closed to hold the nerve inside the channel 1002. Similar to the other embodiments described above, holder 1000 also includes guide posts 1006 to control movement of and electrode array and post holes 1008 that can be filled with material to act as a forward locking catch for the array.

Figure 11B:
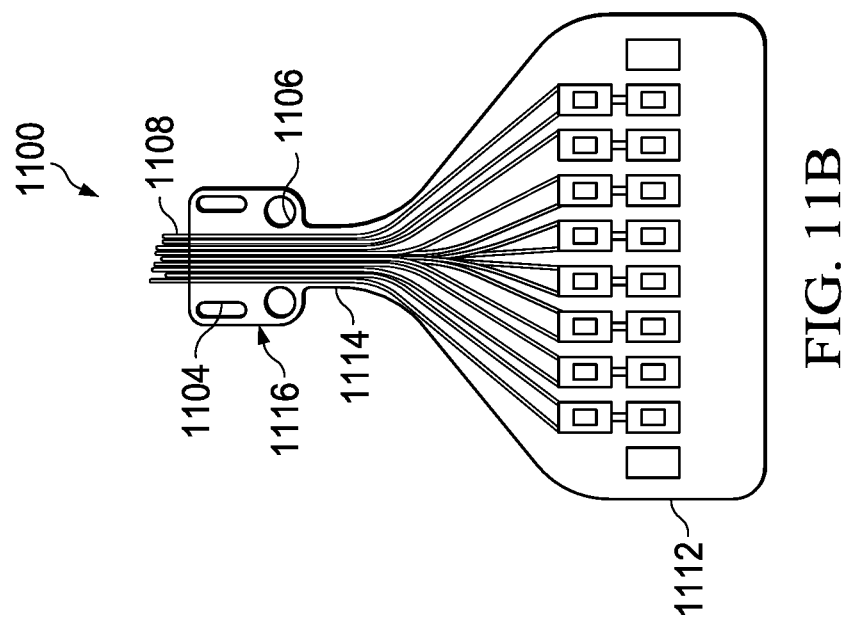
FIG. 11B illustrates a top plan view of the electrode array in accordance with an illustrative embodiment.
Figure 11A:
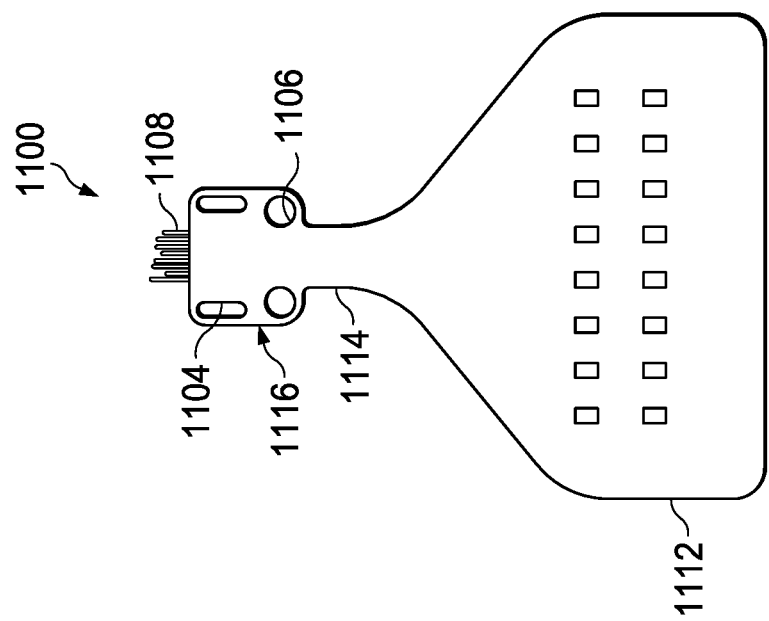
FIG. 11A illustrates a bottom plan view of an electrode array in accordance with an illustrative embodiment.

FIG. 11A illustrates a bottom plan view of an electrode array 1100 in accordance with an illustrative embodiment. FIG. 11B illustrates a top plan view of the electrode array 1100 in accordance with an illustrative embodiment. Electrode array 1100 is an alternate embodiment that comprises similar features as array 400 in FIGS. 4A and 4B including elongate loops 1104, circular loops 1106, and electrode shanks 1108.

However, in this embodiment, the neck 1114 connecting the base 1112 and head 1116 of the array 1100 is significantly shorter than neck 414 of array 400, allowing use of the array 1100 is smaller spaces than array 400.

Figure 12:
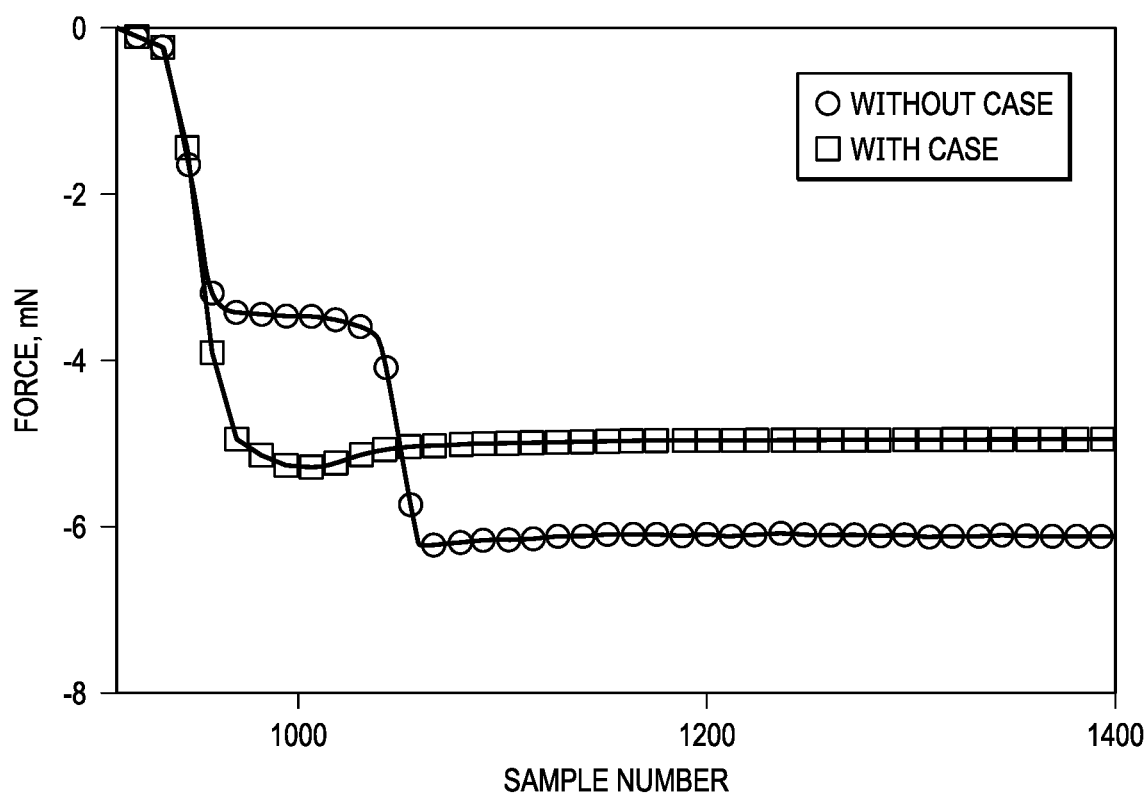
FIG. 12 illustrates a chart comparing buckling force thresholds when not using and when using a nerve holder case in accordance with an illustrative embodiment.

FIG. 12 illustrates a chart comparing buckling force thresholds when not using and when using a nerve holder case in accordance with an illustrative embodiment. The utilization of a nerve holder case structure increases the buckling force threshold ($P_{cr}$), which is the maximum force that an object can tolerate before buckling.

For an 8 µm thick shank with 23 µm width, the buckling force threshold without using a nerve holder case is 3.3 mN. In contrast, with a nerve holder case the $P_{cr}$ of the same size shank is 5.3 mN, a % 60 increase in $P_{cr}$.

Figure 13:
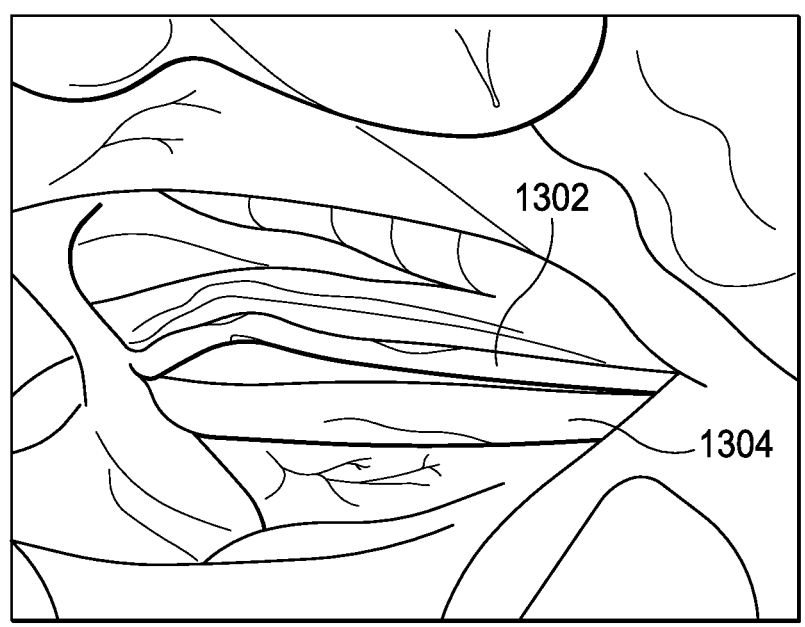
FIG. 13 illustrates a cervical vagus nerve with which the illustrative embodiments can be used.

FIG. 13 illustrates a cervical vagus nerve with which the illustrative embodiments can be used. Vagus nerve 1302 is an illustrative example of a peripheral nerve into which microelectrodes or ultramicroelectrodes can be inserted. In the example shown in FIGS. 13-15, vagus nerve 1302 is in a rat and is separated from the adjacent carotid artery 1304.

FIG. 14 illustrates a nerve held in a nerve holder case before insertion of electrodes in accordance with an illustrative embodiment. In this example application, the shorter electrode array 1100 is being used in conjunction with the nerve holder case 300. As shown, the vague nerve 1302 is held within the channel of case 300. The array 1100 is in the retracted position wherein the shanks 1108 are not inserted into the nerve 1302. Optionally, the array 1108 might be maintained retracted by means of a water-soluble sacrificial layer in the nerve holder case such as Polyvinyl Alcohol (PVA) or Poly(ethylene glycol) (PEG). After the water-soluble sacrificial layer is dissolved the array 1108 can move, guided by posts 106 inserted in elongate loops 1104.

Figure 15:
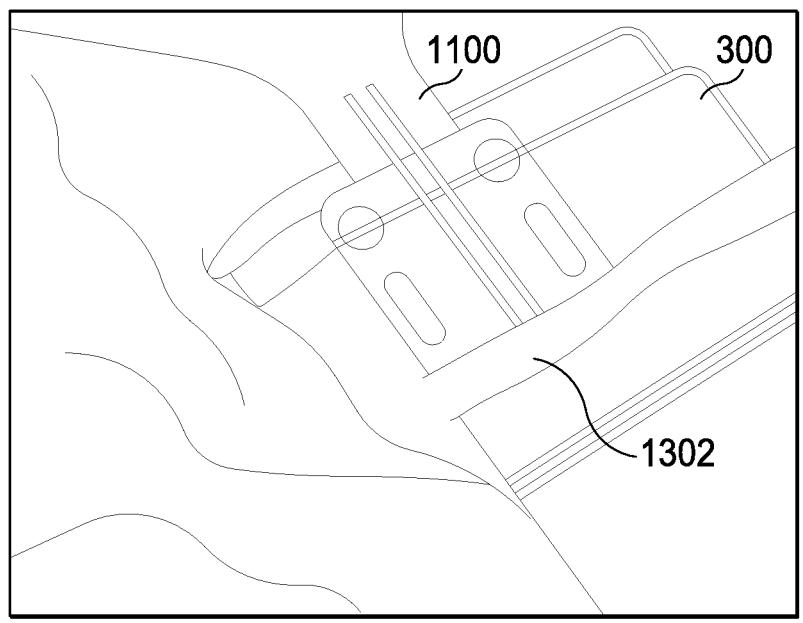
FIG. 15 illustrates a nerve held in a nerve holder case with electrodes inserted in accordance with an illustrative embodiment.

FIG. 15 illustrates a nerve held in a nerve holder case with electrodes inserted in accordance with an illustrative embodiment.

Fabrication Example 1. For the purposes of illustration, one method of fabrication of the nerve case structure is described. The fabrication process is illustrative and not limiting in that those skilled in the fabrication of microelectronic devices and structures will recognize that many different approaches to the fabrication of the nerve holder are possible.

The example nerve holder structure depicted in FIGS. 13, 14, and 15, can be fabricated from SU8 2075 and SU8 2100 (Kayaku Advanced Materials, Inc., MA, USA), an epoxy-based negative photoresist. The process for fabrication and releasing the structures might be as follows: four layers of Omnicoat (Kayaku Advanced Materials, Inc., MA, USA) as a sacrificial layer will be coated on a 100 mm diameter silicon wafer, and each layer soft-baked at 200° C. for three minutes. Three layers of SU8, 100 µm, 250 µm, and 100 µm can be coated on the Omnicoat layers, soft-baked at 65-95° C., exposed to UV-radiation, and post exposure baked at 65-95° C., consecutively.

The thickness of SU8 layers can be custom designed based on the nerve target such that the channel opening and depth are suitable for the nerve target. All layers can be simultaneously developed in the next step by SU8 developer. The wafer is rinsed with isopropyl alcohol (IPA) to wash off the developer. Subsequently, Mf-319 and remover PG can be used to release the structures. MF-319 developer (Kayaku Advanced Materials, Inc., MA, USA) and PG Remover (Kayaku Advanced Materials, Inc., MA, USA) dissolve the Omnicoat layer, which is a sacrificial layer used to facilitate the release of the SU8 structures from the silicon wafer.

The complete device can be produced by assembling a top and a bottom section of the released structures. A UV curing medical device adhesive (Epoxy Technology Inc., MA, USA) can be used to attach the top and bottom parts together.

The narrow channels adjacent to each opening 104 on the lower portion 100 allow a cleaner assembled structure by providing a path for removal of any excess adhesive.

As used herein, the phrase "a number" means one or more. The phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A bioelectric interface, comprising:
a case comprising a channel configured to hold a nerve, wherein the case comprises:
  a lower portion;
  an upper portion; and
  two posts connecting the lower portion and the upper portion;
an electrode array sandwiched between the lower portion and the upper portion, wherein the electrode array is slidably coupled to the case, and wherein the electrode array comprises a number of electrode shanks, and wherein the case restricts movement of the electrode array to one degree of freedom toward or away from the nerve held in the channel and constrains the electrode array to move in one plane for insertion of the electrode shanks into the nerve; and
two elongate loops in the electrode array, wherein the posts are positioned inside the elongate loops to limit a distance the electrode array can slide within the case.

2. The bioelectric interface of claim 1, further comprising:
two circular post holes in a surface of the lower portion; and
two circular loops in the electrode array, wherein the circular loops align with the circular post holes when the electrode array is in a forward position to insert the shanks into the nerve fiber.

3. The bioelectric interface of claim 2, further comprising silicone posts inserted through the circular loops and into the post holes when the electrode array is in the forward position, wherein the silicone posts lock the electrode array in the forward position.

4. The bioelectric interface of claim 1, wherein the upper portion comprises a window through which the nerve and electrode shanks are visible.

5. The bioelectric interface of claim 1, further comprising a water-soluble sacrificial layer in the case that holds the electrode array in a retracted position.

6. A bioelectric interface, comprising:
a lower portion of a case;
an upper portion of the case, wherein the lower portion and the upper portion of the case together enclose a channel configured to hold a nerve;
a number of posts connecting the lower portion and the upper portion; and
at least one electrode array comprising a number of electrode shanks of different lengths, wherein the electrode array is slidably sandwiched between the lower portion and the upper portion of the case, and wherein the case restricts movement of the electrode array to one degree of freedom toward or away from the nerve held in the channel and constrains the electrode array to move in one plane for insertion of the electrode shanks into the nerve; and
a number of elongate loops in the electrode array, wherein each post is positioned inside a respective elongate loop to limit a distance the electrode array can slide within the case.

7. The bioelectric interface of claim 6, further comprising:
a number of circular post holes in a surface of the lower portion; and
a number of circular loops in the electrode array, wherein the circular loops align with the circular post holes when the electrode array is in a forward position to insert the shanks into the nerve.

8. The bioelectric interface of claim 7, further comprising silicone posts inserted through the circular loops and into the post holes when the electrode array is in the forward position, wherein the silicone posts lock the electrode array in the forward position.

9. The bioelectric interface of claim 6, further comprising a water-soluble sacrificial layer in the case that holds the electrode array in a retracted position.

* * * * *